United States Patent [19] [11] 3,956,379
Beaver [45] May 11, 1976

[54] PROCESS FOR RECOVERING NTA
[75] Inventor: Phillip R. Beaver, Baton Rouge, La.
[73] Assignee: Ethyl Corporation, Richmond, Va.
[22] Filed: Oct. 23, 1970
[21] Appl. No.: 83,664

[52] U.S. Cl. .............................................. 260/534 E
[51] Int. Cl.$^2$ .................. C07C 99/12; C07C 101/20
[58] Field of Search ................................. 260/534 E

[56] References Cited
UNITED STATES PATENTS
3,409,666   11/1968   Foreman ......................... 260/534 E OTHER PUBLICATIONS
Marshall et al., Chem. Engr. Prog. 46, (11), 575 (1950), pp. 575–576.

Primary Examiner—Richard L. Raymond
Attorney, Agent, or Firm—Donald L. Johnson; John F. Sieberth; Shelton B. McAnelly

[57] ABSTRACT

It is disclosed that aqueous systems containing the sodium salt of nitrilotriacetate monohydrate (NTA) can be converted into a dry particulate form of NTA of comparatively high bulk density and suitable hygroscopic properties when using a spray drying technique by delivering to the spray dryer an NTA-water mixture which contains a greater amount of NTA than that present in a saturated aqueous solution of NTA. Upon spray drying such a particulate mixture with hot gases in a counter-current or co-current flow under proper conditions, water is removed from the particulate mixture producing a particulate solid NTA product.

7 Claims, No Drawings

… (3,956,379)

PROCESS FOR RECOVERING NTA

BACKGROUND OF THE INVENTION

1. Field of the Invention

This invention relates to the recovery of sodium nitrilotriacetate monohydrate in solid particulate form from mixtures of NTA with water.

2. Description of the Prior Art

Typically sodium nitrilotriacetate monohydrate (NTA) is produced by chemical reaction in an aqueous solution. In use, frequently it is desired to provide product NTA in the form of a particulate mass of comparatively high bulk density and which is free flowing to permit handling and storage without excessive caking and lumping. Although NTA is produced readily in such desirable form by crystallization from solution and centrifugal separation of the crystals from the mother liquor, such processing involves a considerable amount of expensive equipment.

Spray drying of NTA solutions per se is an old technique. It is discussed in U.S. Pat. No. 3,409,666. The spray drying technique for producing particulate NTA from solutions was used in Germany during World War II. Unfortunately, the drying of NTA solutions in a spray dryer generally results in the production of a product comparable in some respects to damp snow in that it has a comparatively low bulk density and it does not flow readily when stored in silos and other bulk handling arrangements. Also it "cakes" excessively when packaged alone or in combination with other materials. Additionally, such material usually is very hygroscopic. Such product characteristics are obtained when feeding NTA solutions of various concentrations, even the more dilute solutions (10–15 wt. percent) which are known to produce spray dried products of a higher density when dealing with many other materials.

SUMMARY OF THE INVENTION

The present invention relates to a process for recovering dry particulate sodium nitrilotriacetate monohydrate, $N(CH_2COONa)_3 \cdot H_2O$ abbreviated NTA, from a mixture thereof with water. Recovered NTA is characterized by having comparatively low hygroscopicity and a comparatively high bulk density. The process comprises forming into a particulate stream a mixture of NTA in water, said mixture containing from about 56 to about 90 percent NTA by weight. Such a mixture is characterized by containing an amount of NTA in excess of that contained by a saturated aqueous solution since the amount of NTA in a saturated solution at a temperature below the boiling point at atmospheric pressure is at most about 53 percent. The particulate stream of NTA and water, preferably hot, near the boiling point at atmospheric pressure, is contacted with a hot gas stream whose temperature is from about 250° to about 1200°F, whereby the water content of the particulate mixture is reduced. Preferably, the total water content is reduced to from about 6.6 to about 7.0 wt. percent, which is only slightly more than the water of hydration, producing a "dry" particulate solid product having a density of from about 0.55 to about 0.85 grams per cubic centimeter. Such a mixture, although apparently dry visually, retains the water of hydration, which is about 6.5 wt. percent of the total.

In a preferred aspect of the process, the mixture of NTA and water contains from about 60 to about 85 wt. percent NTA. A more preferred narrower range is from about 60 to about 70 wt. percent NTA, a particularly preferred composition containing about 68 wt. percent NTA.

In a particularly preferred aspect the present invention employs a hot direct or indirect heated gas stream the temperature of which is from about 400° to about 1000°F, preferably from about 650° to about 900°F. Typically, such a hot gas stream is characterized by a relative humidity ranging from about two to about twenty percent. A typical gas stream temperature is 850°F.

In a preferred aspect the present process produces product NTA having a density from about 0.68 to about 0.80 grams per cubic centimeter. A typical particularly preferred density is about 0.70 grams per cubic centimeter.

The NTA mixtures fed to the spray dryer are obtained in any suitable way. A particularly preferred way is by the evaporation of a part of the water from a feed solution which initially ranges from about 5 percent NTA by weight up to about a saturated solution at the boiling point which contains at most about 53 wt. percent NTA. In this way a mixture is obtained which contains more than a saturation amount of NTA. It is evident that by controlling the extent of evaporation or the amount of water removed therein, one may readily control the concentration of the material fed to spray drying to range from various constituencies described as a slurry, or a paste, etc. One particularly preferred composition is a mixture of about 68 percent NTA because above this percentage, about 70 percent NTA or more, the mixtures are quite viscous so as to make handling difficult, particularly if a nozzle spraying thereof into a chamber is desired. On the other hand, such mixtures as those of 70 percent or more NTA, even "pastes" of the consistency of toothpaste are readily converted into a particulate stream by centrifugal disc apparatus so that the choice in such respects is largely a matter of individual preference, convenience and equipment availability. In general, the centrifugal disc type of apparatus is a preferred arrangement even with feed containing less than 68 percent NTA because it produces a more uniform particle size than does a spray nozzle.

The term "spray dryer" is used to connote a chamber, usually enclosed but essentially open internally wherein the particulate stream to be dried is contacted with heated gas or vapor having less than a saturation amount of water so that enough water is removed from the particles of the stream before they come to rest against a solid surface so that they do not adhere to such solid surface. Various flow arrangements and combinations are used with spray dryers, upflow of heated gas, downflow of heated gas, countercurrent flow of dried product, cocurrent flow of dried product, etc.

The gas used in such spray drying may be any substantially inert gas, such as air, nitrogen, $CO_2$, or in some instances, superheated steam. The gas is heated directly or indirectly as by the combustion of fossil materials such as natural gas, oil or coal or by electrical, steam or other heating through a heat transfer surface device. In general, the gas is heated to a temperature well above the boiling point of water, typically 250°F or higher, but which is below a temperature that will cause decomposition of NTA under the conditions that exist in the system. Thus gas temperatures of up to about 1200°F are usable, where the proportions, length of travel, flow rates, etc. are arranged so that the actual temperatures of the particles do not exceed the decomposition point. In general, it is preferred to use gas temperatures which do not exceed about 900°F to avoid localized overheating.

In a preferred aspect, the present invention relates to a process for recovering NTA from an aqueous system in which the system containing about 68 percent NTA by weight is preheated to a temperature from about 150°F up to about the boiling point thereof at atmospheric pressure, the mixture is then formed into a particulate stream and contacted with a hot gas stream whose temperature is from about 400° to about 1000°F having a relative humidity of from about 2 to about 20 percent. The contacting reduces the total water content of the aqueous system to from about 6.6 to about 7.0 wt. percent including the water of hydration thereby producing a dry particulate solid having a bulk density of from about 0.68 to about 0.80 grams per cubic centimeter with from about 0.1 to about 0.5 wt. percent excess water.

It is preferred to supply the NTA-water feed to the spray dryer at a temperature above ordinary room temperature, preferably near the boiling point at atmospheric pressure. Thus feed temperatures above 150°F are preferred with temperatures of about 200°F being even more preferred.

The source of the NTA used is not of any great criticality. A typical source is by reaction of nitrilotriacetonitrile (NTN) with a caustic such as NaOH or KOH to produce the corresponding metal salt. NTA produced this way may contain various amounts of residual caustic, carbonate or other impurities. In general, volatile impurities are computed as water and non-volatile impurities are computed as NTA in determining the proportions of water and NTA in the feed. In all instances it is preferred that the prior reaction of NTN with caustic be as complete as possible prior to feeding the material to the spray dryer to minimize losses of valuable materials and to minimize contamination of the atmosphere with ammonia should there be any further conversion of nitrile in the spray dryer.

On the other hand, if one chooses deliberately to use the partial hydrolysis technique of U.S. Pat. No. 3,409,666, the teachings of the present invention are generally beneficial in attaining the desired bulk density discussed herein.

Description of the Preferred Embodiments

EXAMPLE I

A mixture of NTA (sodium nitrilotriacetate monohydrate) in water was prepared containing 70 weight percent NTA.

A spray dryer was brought up to temperature using indirectly heated inlet air at 425°F. During the warm-up water was supplied to the centrifugal disc distributor at a rate controlled to maintain an outlet gas temperature of about 220°F. The air flow rate was adjusted.

When the temperatures throughout the dryer became stable, the water feed was changed to a feed of the NTA mixture, supplied to the centrifugal disc at about room temperature (70°F). The mixture feed rate was 130 pounds per hour.

Product was collected and analyzed for bulk density and for total water content. The bulk density was 0.71 gram per cubic centimeter and the excess water above the water of hydration (6.5 weight percent) was 0.4 weight percent.

EXAMPLE II

Example I was repeated using a feed mixture containing 55 weight percent NTA. Inlet gas temperature was 375°F and outlet gas temperature was 225°F. The mixture feed rate was 300 pounds per hour.

The product bulk density was 0.69 gram per cubic centimeter and the excess water content was 0.6 weight percent.

EXAMPLE III

Example I was repeated in a different dryer using a feed mixture containing 61 weight percent NTA and heated to 200°F at a feed rate of 1430 pounds per hour. Inlet gas temperature was 750°F and outlet gas temperature was 260°F. The gas was direct heated using diesel fuel as a heat source. The temperature of the product NTA as collected was 210°F.

The product bulk density was 0.71 gram per cubic centimeter and the excess water content was 0.20 weight percent.

EXAMPLE IV

Example III was repeated using a feed concentration of 65 weight percent and a rate of 1540 pounds per hour.

The product bulk density was 0.81 gram per cubic centimeter and the excess water content was 0.37 weight percent.

EXAMPLE V

Example III was repeated using a feed concentration of 69 weight percent and a rate of 2070 pounds per hour. Inlet gas temperature was 880°F and outlet gas temperature was 248°F.

The product bulk density was 0.77 gram per cubic centimeter and the excess water content was 0.03 weight percent.

EXAMPLE VI

Example III was repeated using a feed concentration of 69 weight percent and a feed rate of 2460 pounds per hour. Inlet gas temperature was 1000°F and outlet gas temperature was 248°F.

The product bulk density was 0.71 gram per cubic centimeter and the excess water content was 0.20 weight percent.

EXAMPLE VII

Example III was repeated using a feed concentration of 65 weight percent, a feed rate of 2100 pounds per hour, inlet gas temperature of 850°F, outlet gas temperature of 250°F, and product temperature of 220°F.

The product bulk density was 0.72 gram per cubic centimeter and the excess water content was 0.12 weight percent.

EXAMPLE VIII

Example I was repeated using another dryer having a spray nozzle atomization and wherein the gas was direct heated using natural gas as a fuel. Mixture feed rate was not measured but feed was at about 70°F. The feed contained 66 weight percent NTA, inlet gas temperature was 720°F, outlet gas temperature was 300°F, and product outlet temperature was 250°F.

The product bulk density was 0.73 gram per cubic centimeter and the excess water content was 0.1 weight percent.

EXAMPLE IX

Example VIII was repeated with an inlet air temperature of 650°F, outlet air temperature of 275°F and product outlet temperature of 200°F.

The product bulk density was 0.71 gram per cubic centimeter and the excess water was 0.1 weight percent.

EXAMPLE X

Example I was repeated using a feed mixture containing 35 weight percent NTA. Inlet gas temperature was 380°F, outlet gas temperature was 270°F, mixture feed temperature was 70°F, and mixture feed rate was 321 pounds per hour.

Product bulk density was 0.35 gram per cubic centimeter. The excess water content was not measured.

EXAMPLE XI

Example VIII was repeated using a centrifugal disc distributor instead of a spray nozzle. The feed concentration was 50 wt. percent NTA. The inlet gas temperature was 500°F and the outlet gas temperature was 265°F.

The product bulk density was 0.52 gram per cubic centimeter and the excess water was 0.5 weight percent.

EXAMPLE XII

Example III was repeated using a feed concentration of 46 weight percent NTA and a feed rate of 2620 pounds per hour.

The product bulk density was 0.53 grams per cubic centimeter and the excess water was 0.8 weight percent.

I claim:

1. A process for recovering NTA from an aqueous system which comprises:
    1. forming into a particulate stream a mixture of NTA in water, said mixture containing from about 56 to about 90 percent NTA by weight, and
    2. contacting said stream with a hot gas stream whose temperature is from about 250° to about 1200°F to reduce the water content of the mixture to produce a dry particulate solid having a bulk density of from about 0.55 to about 0.85 gram per cubic centimeter.

2. The process of claim 1 wherein the said mixture of NTA in water contains from about 60 to about 85 weight percent NTA.

3. The process of claim 1 wherein the mixture contains from about 60 to about 70 weight percent NTA.

4. The process of claim 1 wherein the mixture contains about 68 weight percent NTA.

5. The process of claim 1 wherein the temperature of the hot gas stream is from about 650° to about 900°F.

6. The process of claim 1 wherein the density of the product is from about 0.68 to about 0.80 gram per cubic centimeter.

7. A process for recoverng NTA from an aqueous system which comprises:
    1. preheating to a temperature from about 150°F up to about the boiling point at atmospheric pressure a mixture of NTA in water, said mixture containing about 68 percent NTA by weight,
    2. forming said mixture into a particulate stream, and
    3. contacting said stream with a hot gas stream whose temperature is from about 400° to about 1000°F having a relative humidity of from about 2 to about 20 percent to reduce the total water content of the mixture to from about 6.6 to about 7.0 percent including the water of hydration producing a dry particulate solid having a bulk density of from about 0.68 to about 0.80 gram per cubic centimeter.

* * * * *